United States Patent
Ashe et al.

(10) Patent No.: US 12,178,564 B2
(45) Date of Patent: Dec. 31, 2024

(54) ELECTROMAGNETIC TRACKING AND POSITION MEASUREMENT SYSTEM HAVING INTERFERENCE REDUCTION FROM NEARBY INSTRUMENTATION BY FILTERING TIME-DIVISION MULTIPLEXED SIGNAL VIA STEP FUNCTION

(71) Applicant: Northern Digital Inc., Waterloo (CA)

(72) Inventors: Westley S. Ashe, Hinesburg, VT (US); William Petrow, Charlotte, VT (US)

(73) Assignee: Northern Digital Inc., Waterloo, CA (US)

( * ) Notice: Subject to any disclaimer, the term of this patent is extended or adjusted under 35 U.S.C. 154(b) by 152 days.

(21) Appl. No.: 17/686,112

(22) Filed: Mar. 3, 2022

(65) Prior Publication Data

US 2022/0280060 A1 Sep. 8, 2022

Related U.S. Application Data

(60) Provisional application No. 63/156,695, filed on Mar. 4, 2021.

(51) Int. Cl.
*A61B 5/06* (2006.01)
*A61B 34/20* (2016.01)

(52) U.S. Cl.
CPC .............. *A61B 5/062* (2013.01); *A61B 34/20* (2016.02); *A61B 2034/2051* (2016.02)

(58) Field of Classification Search
CPC . A61B 5/062; A61B 34/20; A61B 2034/2051; G01V 3/08; G08C 15/06;

(Continued)

(56) References Cited

U.S. PATENT DOCUMENTS

| 4,150,284 A | 4/1979 | Trenkler et al. |
| 4,599,561 A | 7/1986 | Takahashi et al. |

(Continued)

FOREIGN PATENT DOCUMENTS

| CN | 111596756 | 8/2020 |
| CN | 111796665 | 10/2020 |

(Continued)

OTHER PUBLICATIONS

MediaTek Inc., "System modeling methodology for reduced-complexity ML/R-ML receivers," 3GPP TSG RAN1 #74bis, R1-134451, Guangzhou, China, Oct. 7-11, 2013, 4 pages.

(Continued)

*Primary Examiner* — Serkan Akar
(74) *Attorney, Agent, or Firm* — Fish & Richardson P.C.

(57) ABSTRACT

An electromagnetic tracking (EMT) system is configured for determining a frequency for generating at least a portion of a magnetic field signal using a transmitter coil of a plurality of transmitter coils. The EMT system configures a time-division multiplexed (TDM) control signal configured to cause the transmitter coil to transmit bursts of the magnetic field signal at the frequency. The EMT system configures a filter for filtering the TDM control signal, the filter configured to shape each burst to reduce or eliminate a harmonic artifact of the bursts. The EMT system causes the transmitter coil to generate the shaped bursts of the magnetic field signal. The EMT system receives, from a sensor, a sensor signal that corresponds to the magnetic field signal, the sensor including the output response indicative of the location of the sensor relative to the transmitter.

21 Claims, 11 Drawing Sheets

(58) Field of Classification Search
CPC . H04L 25/08; H04L 25/03834; H04L 27/264; H04L 27/26412
See application file for complete search history.

(56) References Cited

U.S. PATENT DOCUMENTS

| | | | |
|---|---|---|---|
| 4,945,305 | A | 7/1990 | Blood |
| 5,168,222 | A | 12/1992 | Volsin et al. |
| 5,334,831 | A | 8/1994 | Maurice |
| 5,558,091 | A | 9/1996 | Acker et al. |
| 5,615,229 | A | 3/1997 | Sharma et al. |
| 5,729,129 | A | 3/1998 | Acker |
| 6,043,644 | A | 3/2000 | Coulon et al. |
| 6,172,499 | B1 | 1/2001 | Ashe |
| 6,223,066 | B1 | 4/2001 | Govari |
| 6,236,123 | B1 | 5/2001 | Pinkerton |
| 6,313,624 | B1 | 11/2001 | Alhorn et al. |
| 6,337,627 | B1 | 1/2002 | Von Gutfeld et al. |
| 6,624,626 | B2 | 9/2003 | Khalfin |
| 6,690,963 | B2 | 2/2004 | Ben-Haim et al. |
| 6,762,600 | B2 | 7/2004 | Khalfin |
| 6,836,745 | B2 | 12/2004 | Seiler et al. |
| 6,956,366 | B2 | 10/2005 | Butzmann |
| 7,047,002 | B2 | 5/2006 | Lazoff |
| 7,311,107 | B2 | 12/2007 | Harel et al. |
| 7,441,442 | B2 | 10/2008 | Morgan |
| 7,486,078 | B1 | 2/2009 | Gerald, II et al. |
| 7,538,586 | B2 * | 5/2009 | Sicard ............... H03K 4/00 327/134 |
| 7,912,532 | B2 | 3/2011 | Schmidt et al. |
| 8,121,361 | B2 | 2/2012 | Ernst et al. |
| 8,275,427 | B2 | 9/2012 | Kim et al. |
| 8,305,073 | B2 | 11/2012 | Kather |
| 8,761,679 | B2 | 6/2014 | Wang et al. |
| 9,450,649 | B2 | 9/2016 | Contaldo et al. |
| 9,492,639 | B2 | 11/2016 | Clark et al. |
| 9,610,016 | B2 | 4/2017 | Shusterman |
| 9,797,238 | B2 | 10/2017 | Frosell et al. |
| 10,050,677 | B1 | 8/2018 | Thoen |
| 10,230,428 | B1 | 3/2019 | Barzegar et al. |
| 10,243,440 | B2 | 3/2019 | Copeland, Jr. |
| 2003/0016006 | A1 | 1/2003 | Khalfin |
| 2003/0135112 | A1 | 7/2003 | Ritter et al. |
| 2004/0090226 | A1 | 5/2004 | Khalfin |
| 2004/0254453 | A1 | 12/2004 | Govari |
| 2005/0285591 | A1 | 12/2005 | Higgins et al. |
| 2006/0122516 | A1 | 6/2006 | Schmidt et al. |
| 2007/0057668 | A1 | 3/2007 | Lee et al. |
| 2013/0080085 | A1 | 3/2013 | Von Herzen et al. |
| 2014/0333295 | A1 | 11/2014 | Fernandez et al. |
| 2016/0142106 | A1 | 5/2016 | Pernisek et al. |
| 2016/0169717 | A1 * | 6/2016 | Zhitomirsky .......... G01D 5/142 702/94 |
| 2016/0226560 | A1 | 8/2016 | Dent |
| 2016/0246369 | A1 | 8/2016 | Osman |
| 2018/0241094 | A1 | 8/2018 | Hintergerger et al. |
| 2019/0290151 | A1 | 9/2019 | Shastri et al. |
| 2019/0356178 | A1 * | 11/2019 | Widmer ............... G01R 33/028 |

FOREIGN PATENT DOCUMENTS

| | | |
|---|---|---|
| CN | 111830444 | 10/2020 |
| WO | WO 2003029921 | 4/2003 |

OTHER PUBLICATIONS

Xiangming et al., "Measurement System for Short-Time and Frequency-Conversion Magnetic Field Radiated by High-Power Electromagnetic Equipment," Transactions of China ElectroTechnical Society, 25(9):1-6 (English Abstract only).

* cited by examiner

1000

Obtain threshold data representing a threshold interference level for a remote system in an environment of the electromagnetic tracking system  1002

Configure a filter for filtering the TDM control signal to reduce the harmonic artifact of the bursts below the threshold interference level represented in the threshold data  1004

ELECTROMAGNETIC TRACKING AND POSITION MEASUREMENT SYSTEM HAVING INTERFERENCE REDUCTION FROM NEARBY INSTRUMENTATION BY FILTERING TIME-DIVISION MULTIPLEXED SIGNAL VIA STEP FUNCTION

CLAIM OF PRIORITY

This application claims priority under 35 U.S.C. § 119(e) to U.S. Patent Application Ser. No. 63/156,695, filed on Mar. 4, 2021, the entire contents of which are hereby incorporated by reference.

TECHNICAL FIELD

This disclosure relates to electromagnetic tracking systems. More specifically, this disclosure relates to reducing interference with nearby instrumentation in a tracking environment.

BACKGROUND

Electromagnetic Tracking (EMT) systems are used to aid in locating instruments and anatomy in medical procedures. These systems utilize a magnetic transmitter in proximity to a magnetic sensor. The sensor can be spatially located relative to the transmitter.

SUMMARY

An Electromagnetic Tracking (EMT) system can be used to track the position and/or orientation of a sensor (e.g., the pose) relative to a transmitter. The EMT system is configured to transmit tracking signals including time-division multiplexed (TDM) alternating current (AC) signals. This includes transmitting sinusoid pulses or bursts from each of a plurality of transmitting coils by cycling each transmitter ON and OFF. The EMT system includes a receiver configured to receive the sinusoid pulses or bursts. A coil in the receiver produces a signal in response to receiving the transmitted signal. The signal produced by the receiver is associated with one of the transmitters. Based on receiver signals representing each of the transmitted signals, the EMT system can determine an approximate pose of a tracked object at the location of the receiver.

For transmission of the TDM-AC signal, the EMT system multiplies a shaping signal with the sine burst signal. The shaping signal is used to alternate each transmitter between the ON state and the OFF state. The EMT system forms the shaping signal to create a signal envelope for the sine burst. Rather than a square-wave shaping signal, the EMT system is configured to produce a shaping signal that ramps up from OFF to fully ON and ramps down from fully ON to OFF. The EMT can form the shaping signal by applying one or more filters to the shaping signal. The shaping signal enables the transmitter to transmit a sine burst having a maximum signal amplitude for a period of time while also reducing transmitted harmonic signals resulting from cycling between OFF and ON states at a particular frequency. The exact shape of the shaping signal is tuned to reduce the harmonic signal amplitude while also preserving the sine burst amplitude such that the sine burst is strong enough to generate a signal at the receiver.

The EMT system includes sensor coils having magnetic core designs. These cores can be smaller relative to air-cores that are linear while still producing a relatively strong signal suitable for tracking purposes such as for use in medical catheters. The relative smaller size of the receiver having a coil with a magnetic core enables the receiver to be smaller than the receiver would be using coils with air cores, which produce a linear response but generally require a relatively stronger transmitted signal.

The EMT system uses TDM-AC transmitted signals that are shaped as previously described to enable use of smaller, non-linear receiver coils in the receiver. This combination of features provides one or more of the following advantages. The EMT system does not cause intermodulation distortion (IMD) in the coils of the receiver. This is because, rather than transmitting EM signals at multiple frequencies using a division multiplexed (FDM)-based transmission, the EMT system transmits EM signals using TDM-AC-based transmissions.

IMD can cause tracking errors in the EMT system. The use of TDM-AC signals allows the use of magnetic cores (which provide a stronger response than air cores) in receive coils. The use of shaped TDM-AC signals by the EMT system reduces or eliminates harmonic signals (e.g., transmitted signals that are at different frequencies than the sinusoid burst frequency—also called a center frequency or selected frequency). As previously described, the harmonic frequencies are an artifact of cycling the transmitters between OFF and ON states to perform TDM-AC transmission.

The shaping signal causes the transmitters to "ramp up" and "ramp down" transmission of the respective TDM-AC signals. The shaping signal reduces the strength of transmitted harmonic frequencies while preserving signal strength for the selected center frequency. The reduction in the strength of transmitted harmonic signals reduces interference that may occur with the operation of nearby electronic instrumentation, such as electrocardiographs (EKGs) that are normally sensitive to signals below 1 KHz, or for other biomedical instrumentation (e.g. medical impedance location devices), which are generally susceptible to noise above 10 KHz.

Additionally, the shaped signal prevents induced IMD in EMT ferrite-core sensors due to the harmonics of the TDM-AC waveform (i.e., a sinusoid pulse or burst). This preserves EMT system performance. The shaped transmitter signals benefit overall EMT system performance (e.g., system noise) by reducing the effects of IMD in EMT ferrite-core sensor inputs.

The one or more advantages and/or features previously described can be realized by one or more of the following embodiments.

In an aspect, a system includes a transmitter that includes a plurality of coils. The transmitter is configured to generate magnetic field signals. The system includes a sensor that includes a receiver coil. The sensor is configured to provide sensor signals that correspond to the magnetic field signals generated by the transmitter. The sensor signal is configured to produce an output response indicative of the location of the sensor relative to the transmitter based on the magnetic field signals generated by the transmitter. The system includes a computing device in communication with the transmitter and the sensor. The computing device is configured to determine a frequency for generating at least a portion of a magnetic field signal using a transmitter coil of the plurality. The computing device is configured to configure a time-division multiplexed (TDM) control signal for controlling transmissions of the magnetic field signal from the transmitter coil, the TDM control signal configured to cause the transmitter coil to transmit bursts of the magnetic field signal at the frequency. The computing device is configured to configure a filter for filtering the TDM control signal, the filter configured to shape each burst to reduce or eliminate a harmonic artifact of the bursts. The computing device is configured to cause the transmitter coil to generate the shaped bursts of the magnetic field signal. The computing device is configured to receive, from the sensor, a sensor signal that corresponds to the magnetic field signal, the sensor signal including the output response indicative of the location of the sensor relative to the transmitter.

In some implementations, the filter comprises a low-pass filter that filters a step function and wherein the computing device is further configured to multiply the magnetic field signal with the step function to shape the bursts.

In some implementations, the magnetic field signal comprises a TDM alternating current (TDM-AC) signal.

In some implementations, the receiver coil comprises a core that has a relative magnetic permeability value greater than 1. In some implementations, the core comprises one of a ferrite material or a permalloy material.

In some implementations, each coil of the plurality of coils in the transmitter is configured to generate a respective magnetic field signal at a respective frequency value that is different from the other coils of the plurality. In some implementations, the respective magnetic field signal of each coil is shaped by a filter signal to prevent interference of the respective magnetic field signal of each coil with adjacent measurement modalities of the other coils of the plurality.

In some implementations, the sensor signal comprises a voltage that is generated based on interaction between the sensor and the magnetic field signal generated by the transmitter. In some implementations, a value of the voltage is indicative of at least one of an orientation and a position of the sensor relative to the transmitter.

In some implementations, filter is configured to reduce the harmonic artifacts received at another electronic device in the environment to below a threshold level specified for the other electronic device.

In some implementations, the sensor is selected from a group comprising: a hall-effect sensor, a magnetoresistive sensor, a magneto-optical sensor, and a fluxgate magnetometer.

In a general aspect, a method for reducing interference caused by a magnetic tracking system includes determining a frequency for generating at least a portion of a magnetic field signal using a transmitter coil of a plurality of transmitter coils. The method includes configuring a time-division multiplexed (TDM) control signal for controlling transmissions of the magnetic field signal from the transmitter coil, the TDM control signal configured to cause the transmitter coil to transmit bursts of the magnetic field signal at the frequency. The method includes obtaining threshold data representing a threshold interference level for one or more devices in an environment of the magnetic tracking system. The method includes configuring a filter for filtering the TDM control signal, the filter configured to shape each burst to reduce a harmonic artifact of the bursts below the threshold interference level of the threshold data. The method includes causing the transmitter coil to generate the shaped bursts of the magnetic field signal. The method includes receiving, from a sensor, a sensor signal that corresponds to the magnetic field signal, the sensor including the output response indicative of the location of the sensor relative to the transmitter.

In some implementations, the threshold data are obtained from the one or more other devices during operation of the magnetic tracking system, and wherein the filter is configured to shape each burst for a next transmission in response to obtaining the threshold data.

In a general aspect, a method includes determining a frequency for generating at least a portion of a magnetic field signal using a transmitter coil of a magnetic tracking system. The method includes configuring a time-division multiplexed (TDM) control signal for controlling transmissions of the magnetic field signal from the transmitter coil, the TDM control signal configured to cause the transmitter coil to transmit bursts of the magnetic field signal at the frequency. The method includes configuring a filter for filtering the TDM control signal. The filter is configured to shape each burst to reduce or eliminate a harmonic artifact of the bursts. The method includes causing the transmitter coil to generate the shaped bursts of the magnetic field signal. The method includes receiving, from a sensor of the magnetic tracking system, a sensor signal that corresponds to the magnetic field signal, the sensor signal including the output response indicative of the location of the sensor relative to the transmitter.

In some implementations, the filter comprises a low-pass filter that filters a step function. The method further includes multiplying the magnetic field signal with the step function to shape the bursts.

In some implementations, the magnetic field signal comprises a TDM alternating current (TDM-AC) signal. In some implementations, a receiver coil of the sensor includes a core that has a relative magnetic permeability value greater than 1. In some implementations, the core includes one of a ferrite material or a permalloy material.

In some implementations, the filter is configured to reduce the harmonic artifacts received at another electronic device in the environment to below a threshold level specified for the other electronic device.

In some implementations, the sensor is selected from a group comprising: a hall-effect sensor, a magnetoresistive sensor, a magneto-optical sensor, and a fluxgate magnetometer.

The details of one or more embodiments of the subject matter described herein are set forth in the accompanying drawings and the description below. Other features, objects, and advantages of the subject matter will be apparent from the description and drawings, and from the claims.

DETAILED DESCRIPTION

An EMT system includes a system configured to track a location of an object in an environment. For example, the EMT system can be used in surgical settings to track a piece of medical equipment, a robotic arm, etc., thereby allowing its respective three-dimensional (3D) location and orientation to be known to a medical professional (e.g., a surgeon) during a medical procedure. Such electromagnetic tracking can be used for guidance purposes in image-guided procedures, and in some cases may allow for reduced reliance on other imaging modalities, such as fluoroscopy, which can expose the patient to health risk of ionizing radiation.

In general, a transmitter having one or more coils is configured to generate an alternating current (AC) EM field. A sensor having one or more coils that is in proximity to the generated EM field is configured to measure characteristics of the generated EM field. The measurements are based on the position and orientation of the sensor relative to the transmitter. For example, when the sensor is located at a particular position and orientation, the EM field at that particular location may have particular characteristics. The sensor can measure the characteristics of the EM field and provide such measurements to a computing device in the form of a sensor signal. Using information related to the generated EM field and the sensor signal received from the sensor, the computing device can determine the position and/or orientation of the sensor (and, e.g., the position and/or orientation of a medical device in which the sensor is incorporated).

Figure 1:
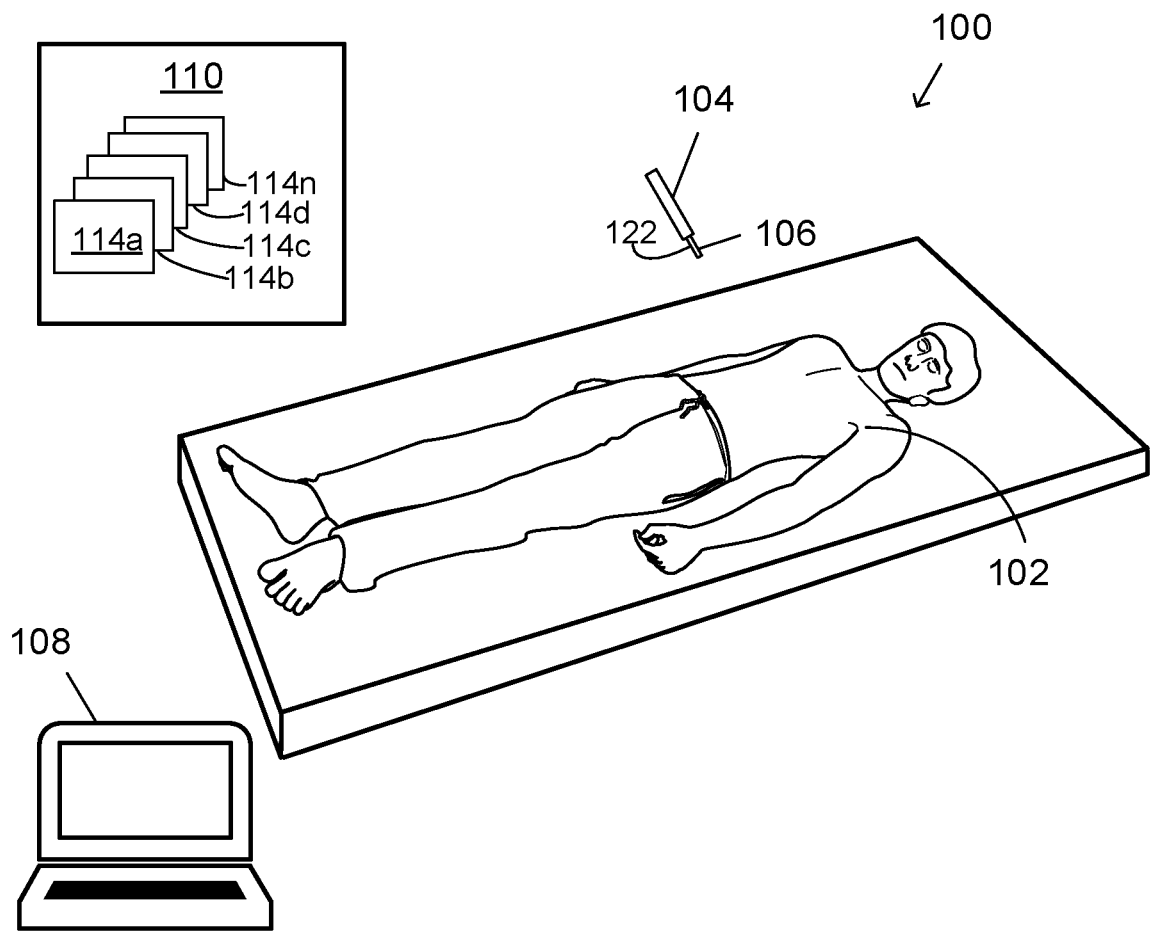
FIG. 1 is an illustration of an EMT system that includes a sensor and a transmitter.

Generally, a plurality of transmitter coils are included in the transmitter of the EMT system to increase the tracking degrees of freedom (DoF), as further described in reference to FIG. 1. The EMT system is configured to avoid distortions, such as intermodulation distortion (IMD) in the receiver coil(s) caused by transmitting at multiple frequencies during frequency division multiplexed (FDM) operation. To avoid distortions such as IMD distortion that can occur in FDM based systems, the EMT system is configured to operate using time-division multiplexed alternating current (TDM-AC) transmissions.

To receive the TDM-AC transmissions, EMT sensor coils can include magnetic cores. The magnetic (e.g., ferrite, permalloy, etc.) core of the coil increases the sensitivity of the receiver coil in comparison with an air core for the sensor coil. A response signal generated by the sensor coil includes a signal produced by the receiver coil in response to receiving a magnetic signal from the transmitter coil(s). A linear response includes an output signal that is based on a linear function of the input signal. A non-linear response includes an output signal that is a non-linear function of the input signal.

Sensor coils including an air core design are relatively large (e.g., compared to sensor coils including metal cores). The relatively large size of sensors including coils with air cores is impractical for some purposes, such as use with various medical catheters. In contrast, the sensor of the EMT system can be relatively smaller using a non-linear core, such as a magnetic core (e.g., a metal with a relative magnetic permeability value substantially above 1). Non-linear cores can include ferrite cores, permalloy cores, and similarly magnetic materials as core materials.

Non-linear cores can provide a relatively strong inductive response in a receiver coil of the sensor, enabling the sensor to be more sensitive to transmitted TDM-AC signals. When operating using TDM-AC transmissions, harmonic signals of the TDM-AC transmitted frequencies may be detectable by nearby electronic instrumentation as unwanted noise. The harmonic signals can be artifacts of the cycling of the transmitters between ON and OFF states for the TDM-AC transmission. The signal harmonics may interfere with the operation of nearby electronic instrumentation. For example, equipment, such as electrocardiographs (EKGs) that are normally sensitive to signals below 1 kilohertz (KHz), can experience interference. In another example, biomedical instrumentation devices, such as medical impedance location devices, which are generally susceptible to noise above 10 KHz can experience interference.

To reduce or eliminate the harmonic signal artifacts, the EMT system applies a shaping (or modulating) excitation signal to limit (e.g., spectrally) the emitted magnetic signals of the EM transmitters. The modulated or shaped excitation signal minimizes or eliminates interference with other biomedical instrumentation in the tracking environment by limiting the signal strength of the harmonic signals. The shaping signal causes an amplitude of the sine burst to ramp up and ramp down during each TDM cycle, rather than a near-instantaneous OFF/ON switching of a square wave excitation signal. The exact shape of the shaping signal depends on receiver sensitivity and the particular application for the tracking being performed.

FIG. 1 presents an exemplary embodiment of the EMT system 100, which can be used for image-guided medical procedures performed on a patient 102. The EMT system 100 may include a freely moving medical instrument, which is a tracked object 104 by the EMT system. The tracked object 104 can include any manner of surgical tools and devices for use in medical treatment. The EMT system 100 permits targeting of an anatomical organ, structure, or vessel for visualization, diagnostic, interventional purposes, etc. Instruments for use in the EMT system 100 typically include one or more magnetic sensors including one or more coils. The sensor 106 may be embedded in a channel or affixed to a tip of the tracked object 104. The particular sensor 106 employed by the EMT system 100 may be determined by the procedure type and/or the measurement performance requirements. In the illustrated example, the sensor 106 is connected to an electronic unit or a computing device, such as a processing device 108, via a wireless connection. Under control of circuitry for energizing magnetic fields, the sensor 106 measures its instantaneous position (x, y, z) and orientation angles (azimuth, altitude, roll) in three-dimensional space relative to a transmitter 110 and sends the measurement signal to the processing device 108 for analysis.

Generally, the sensor 106 can include a magnetic core for the receiver coil 122. The magnetic core includes a high magnetic permeability relative to the surrounding air, and thus results in a stronger inductive response at the coil. This enables the receiver coil 122 to operate in lower-energy environments or be reduced in size to create a response signal that is useful for magnetic tracking. For example, a ferrite core (or other metal) can be used in the sensor 106 to reduce size of a receive coil of the sensor relative to an air core for a receive coil. The reduced size can be useful for including a smaller sensor 106 in some medical instruments that may be tracked objects 104. For example, ferrite core receivers are used in the sensor 106 for use inside or near a patient, such as for a catheter, endoscope, or other such medical instrument.

Like the sensor 106, the particular transmitter employed by the EMT system 100 may be determined by the procedure type, measurement performance requirements, etc. In an example, the transmitter 110 may be a three-axis magnetic transmitter that includes three transmitter coils—an X-coil for generating an X-component of an EM field, a Y-coil for generating a Y-component of the EM field, and a Z-coil for generating a Z-component of the EM field. That is, each transmitter coil 114a-n is configured to provide a portion of the EM field. In some implementations, the transmitter coils are formed as a concentric, collocated set of transmitter coils 114a-n.

Additional transmitter coils 114a-n are added to add degrees of freedom for tracking the tracked object 104. For example, fourth and fifth coils can be added for detecting pitch and yaw of the tracked object 104. To achieve increased tracking accuracy, there can include more than five transmitter coils 114a-n. For example, six, seven eight, or up to twelve or more transmitter coils 114a-n can be used. Additional transmitter coils 114a-n may increase precision of the EMT system 100.

The transmitter 110 is typically fixed in space beside, above, or beneath the patient or on medical equipment, where it acts as the reference frame for the measurements provided by the sensor 106. In some implementations, the transmitter 110 may be designed to minimize and/or negate the effect of distorters beneath its surface, such as procedural tables and/or equipment. The measurements provided by the sensor 106 and transmitter 110 provide sufficient information to navigate the instrument 104 outside or within the body of the patient 102 for diagnostic and interventional purposes, in some cases while providing visual feedback.

In some implementations, the processing device 108 is an imaging computer that is configured to provide imaging capabilities to the EMT system 100. The imaging processing device 108, which in the illustrated example is in wireless communication with the sensor 106 and transmitter 110, is configured to store pre-acquired or intra-operative images of the patient 102 in an image database. Such images may then be input to imaging software for registration and visualization purposes. During the medical procedure, the three-dimensional location of the instrument 104 can be tracked relative to the anatomy of the patient 102 and the pre-acquired or inter-operative images and shown in real time on a display of the processing device 108. When the instrument 104 is advanced toward the target of interest within the body of the patient 102, the transmitter 110 can be activated and energized, thus producing measurable signals (e.g., voltage signals) in the sensor 106. These signals are processed and the three-dimensional location is computed for transmission to the processing device 108. In some implementations, the processing device 108 includes a guidance electronics unit that is configured to process the voltages in order to provide the three-dimensional location.

In some implementations, before the start of the procedure, one or more protocols are implemented. One protocol may initialize the instrument 104 and sensor 106 to prepare for tracking by the processing device 108. Configuration data, such as instrument type, part number, sensor location in the instrument, calibration data, etc. may be stored in a memory of the processing device 108. From this point forward, the EMT system 100 may automatically provide the imaging software with specific configuration of the attached instrument 104. In such implementations, no manual entry of medical instrument data by the physician may be required. Another protocol may correlate the instrument 104, imaging modality, and patient reference frames so that the physician can guide the instrument intuitively within the patient 102 by following three-dimensional visualization cues. Once these protocols have been accomplished, the processing device 108 can continuously receive instrument guidance data at the patient 102 and align the data with locations on the display of the processing device 108. In this manner, as the physician moves the tracked object 104 (e.g., a medical instrument) to a target within the body of the patient 102, the physician also sees an image on the display of an icon that corresponds to the instrument 104 relative to target images of the patient 102. The control of the guidance data and integration with scanned images may be a function of the three-dimensional software operable on the processing device 108.

In general, the EM field generated by the transmitter 110 has characteristics that can be measured by the receive coils of the sensor 106. For example, as the sensor 106 changes position in proximity to the transmitter 110, the x-, y-, and z-coils can each measure characteristics of the X-component, the Y-component, and the Z-component of the EM field, providing nine total components of the sensor signal. A matrix representation of the sensor signal is sometimes referred to as an S-matrix (e.g., a 3×3 matrix) in which the columns represent the X-, Y-, and Z-coils of the transmitter 110 and the rows represent the x-, y-, and z-coils of the sensor 106.

The receiver coil 122 of the sensor 106 has a non-linear response, as previously described, because the coil has a magnetized core (e.g., a ferrite core or other magnetized metal core). For example the materials can include ferrite materials, a permalloy, or other similar material. In generally, a relatively long and narrow magnetized material (e.g., having a length to width ratio greater than 1) can be used for the core of the receiver coil 122 of the sensor 106. In another example, a non-linear core material having other shapes (e.g., a cube) can be used for the core of the receiver coil. The EMT system 100 uses time-domain multiplexing to control transmitted EM signals from each of the transmitter coils 114a-n of the transmitter 110. For example, the transmitter 110 can include an X-coil operating at carrier frequency A, a Y-coil is operating at carrier frequency B, and a Z-coil can operate at carrier frequency C.

In some implementations, the sensor 106 includes other types of non-linear sensing elements configured to measure magnetic field strength/magnetic flux density of the transmitted signal for determining the position of the sensor relative to the transmitter 110. For example, the sensor 106 can include a hall-effect sensor. In another example, the sensor 106 includes a magnetoresistive sensor configured to measure a changing resistance of a material under the influence of magnetic fields. In another example, the sensor 106 includes a magneto-optical sensor. In another example, the sensor includes a fluxgate magnetometer. Each of these devices can have a non-linear response to the transmitted magnetic signal.

Each coil is configured for emitting TDM-AC signals. These signals can each include a sinusoid pulse or burst. The EMT system 100 applies a bandwidth-limiting window function to each EM transmitter signal burst or sinusoid pulse. The window function reduces the spectral spread from the center frequency of the transmission. The window function is configured to eliminate signal harmonics and therefore reduce or eliminate interference with other medical devices and/or equipment, as previously described.

The shaping of the excitation signal performed by the EMT system 100 is now described. To operate the transmitter 110, a filter is placed on each coil drive of the transmitter. This filter shapes each sine pulse or burst during the TDM-AC transmission for a transmitter. The controller of the EMT system 100 causes a square wave (e.g., ON/OFF) control signal to be sent to the transmitter coils 114a-n to control how the coils of the transmitter 110 transmit the carrier signal. The square wave control signal is shaped by the filter to cause the signal to ramp up from OFF to ON and ramp down from ON to OFF. The shaped signal reduces a rate of change of the excitation signal between the OFF and ON portions of the signal. The reduced change causes the amplitude of harmonic artifacts of the TDM-AC transmission to be reduced or eliminated. This reduces distortion in tracking the tracked object 104 because the sensor 106 does not receive the harmonic artifacts (or receives artifacts of reduced amplitude) that can interfere with tracking.

The coils of the transmitter 110 thus each transmit a waveform composed from several elements. A signal is transmitted at a desired frequency (sometimes called a center frequency). In an example, the frequency can be about 3200 Hz, though the EMT system 100 can adjust the frequency to other values. The signal is shaped by the control signal (or excitation signal) by multiplying the signals. The EMT system 100 applies a filter to the control signal, which is originally a square wave. The filter controls how quickly or slowly the sine wave amplitude is ramped up and down for each cycle. The faster the transmitter is turned completely on and off for each cycle, the higher the root-mean-squared (RMS) signal strength value is at the desired frequency. A stronger signal is easier to distinguish from noise by the receiver coil(s) of the sensor 106. Each coil of the transmitter 110 thus transmits a signal within a "signal envelope" shaped by the filtered control signal. Examples of these shaped signals are subsequently described in reference to FIGS. 2-4.

The shaped signals reduce harmonic artifacts of the transmitted TDM-AC signals. The receiver coils of the ETM system 100, which have increased sensitivity due to their magnetic cores, can receive the TDM-AC signal and distinguish the desired frequency from noise of the environment and the harmonic artifacts, now reduced in amplitude. This configuration bypasses the problem of IMD that would be caused in the receiver coils if a FDM approach were used in the EMT system 100.

The filter used to shape the transmitted signals from the respective transmitter coils 114a-n can be configured based on the parameters of the non-linear core of the receiver coil 122 of the sensor 106. In some implementations, the EMT system 100 adjusts the size of the envelope based on the permitted signal strength of the harmonic artifacts. The EMT system 100 can increase the RMS signal level of the transmission by the transmitting coils 114a-n by decreasing an amount of time needed to switch from the OFF state to the ON state, or vice versa. This also increases the strength of the harmonic artifacts. If the amplitudes of the harmonic artifacts are below a threshold for the receiver coil 122, the RMS signal level can be increased, which enables a stronger signal transmission at the selected frequency of the sine burst. This tuning can be performed to ensure that the transmitted signal is strong enough for use in operation of the EMT system 100 in a particular environment and to ensure that the harmonic artifact threshold is not exceeded in a given receiver coil 122. For example, the signal strength may be increased by the EMT system 100 for operation at greater ranges between the transmitter 110 and the sensor. In some implementations, the signal strength may be increased for operation in the presence of other distortions to the signal. In a specific example, the EMT system 100 is configured to communicate with one or more other systems in the environment of the EMT system. The one or more other systems or devices may send information describing interference thresholds for their respective operations. The information represents a maximum tolerable signal strength at one or more frequencies corresponding to the harmonic signal before the other system or device experiences degraded performance from the interference. In response, the EMT system 100 is configured to adjust the envelope to reduce interference below the received threshold levels while still maximizing the signal strength. In some implementations, the EMT system 100 adjusts the signal envelope in real time or near real time (e.g., adjusts for a subsequent transmission cycle) based on the obtained threshold information. In some implementations, the EMT system 100 stores the threshold information for one or more other devices and retrieves that information for use during envelope construction at a later time (e.g., subsequent operations).

The EMT system 100 causes each transmitter coil 114a-n of the transmitter 110 to transmit a shaped signal that is configured to avoid interference with adjacent measurement modalities. The sensor 106 is configured to receive the signals from the respective transmitter coils 114a-n of the transmitter 110 without harmonic artifacts or with a minimized harmonic artifact that does not result in tracking errors or interference with other systems in the tracking environment. For example, for a twelve transmitter coil system, the sensor 106 is configured to receive twelve signals at twelve respective frequencies. Each of these transmissions is shaped so that the harmonic artifacts avoid interference with the other transmissions. If more coils are included in the transmitter 110, a size of each shaped envelope for each transmission can be reduced to avoid interference with adjacent modalities while maintaining sufficient signal strength for the selected frequency.

Figure 2:
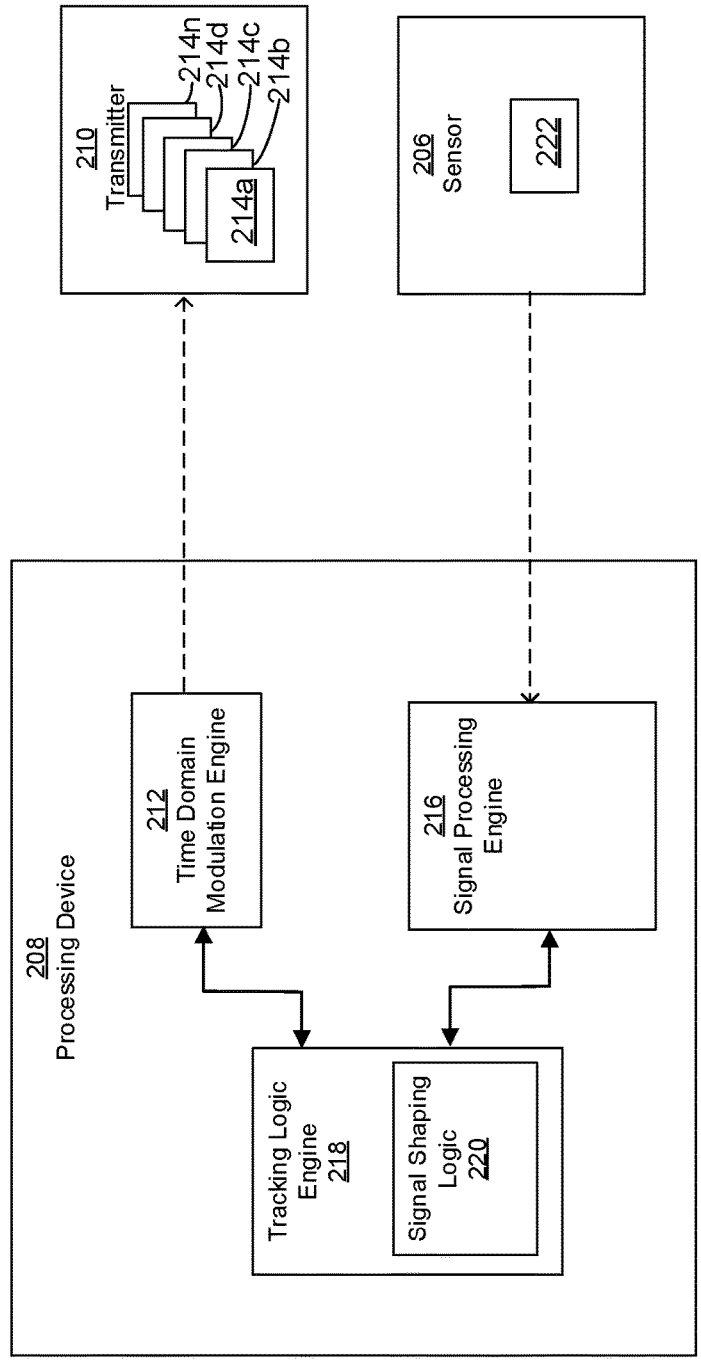
FIG. 2 shows a block diagram of the EMT system of FIG. 1.

Turning to FIG. 2, a block diagram of the EMT system 200 is shown. The EMT system 200 can be substantially similar to the EMT system 100 described in reference to FIG. 1. The processing device 208 of the EMT system 200 can include a tracking logic engine 218, a TDM engine 212, and a signal processing engine 216. The tracking logic engine 218 is configured to determine an approximate position and orientation of the tracked object 204 based on signals received from the sensor 206. As previously described, the signals received from each of the transmitter coils 214a-n of the transmitter 210 are transmitted to the sensor 206. The sensor 206 receives the transmitted signals with a receiver coil 222 that is generally non-linear. The sensor 206 is configured to send the measured signals to the processing device 208, typically over a wireless communications link. The processing device 208 receives the measured signals from the sensor 206 at the signal processing engine 216. The signal processing engine 216 is configured to receive the signal from the sensor and send a digital representation of the signal to the tracking logic engine 218. The tracking logic engine 218 determines the position and orientation of the tracked object 204 in the environment of the EMT system 200 based on parameters of the EMT system, such as which transmitter coil 214a-n is associated with the received signal, hardware calibration parameters of the system, known environmental distortions (if any), and so forth.

The tracking logic engine 218 includes signal shaping logic 220. The signal shaping logic 220 is configured to shape the transmission from each transmitter coil to reduce or eliminate harmonic artifacts, as previously described. The signal shaping logic controls what filter parameters are used to drive the transmitted signals from each of the transmitter coils 214a-n.

The TDM engine 212 is configured to multiply the shaping signal with the sinusoid signals generated by each of the transmitter coils. The TDM engine 212 causes each transmitting coil to transmit shaped sinusoid bursts that are shaped to reduce or eliminate harmonic artifacts, as previously described. The TDM engine 212 controls the transmitter coils so that each transmitter coil operates in turn. The TDM engine cycles through the transmitter coils so that each transmitter coil 214a-n transmits a shaped burst for each transmission cycle to be received by the receiver coil 222.

As previously described, the transmitter coils 214a-n each transmit a shaped signal including a sine pulse having a particular frequency. The number of transmitter coils 214a-n can vary depending on the precision required for tracking the tracked object 204. The number of transmitter coils 214a-n can include 5, 6, 8, 12, or more.

As previously described, the receiver coil 222 of the sensor 206 is generally non-linear. The non-linear receiver coil 222 of the sensor 206 can be smaller than linear coils with similar response sensitivity. The receiver coil 222 can include a magnetic core, as previously described in relation to FIG. 1.

Figure 3:
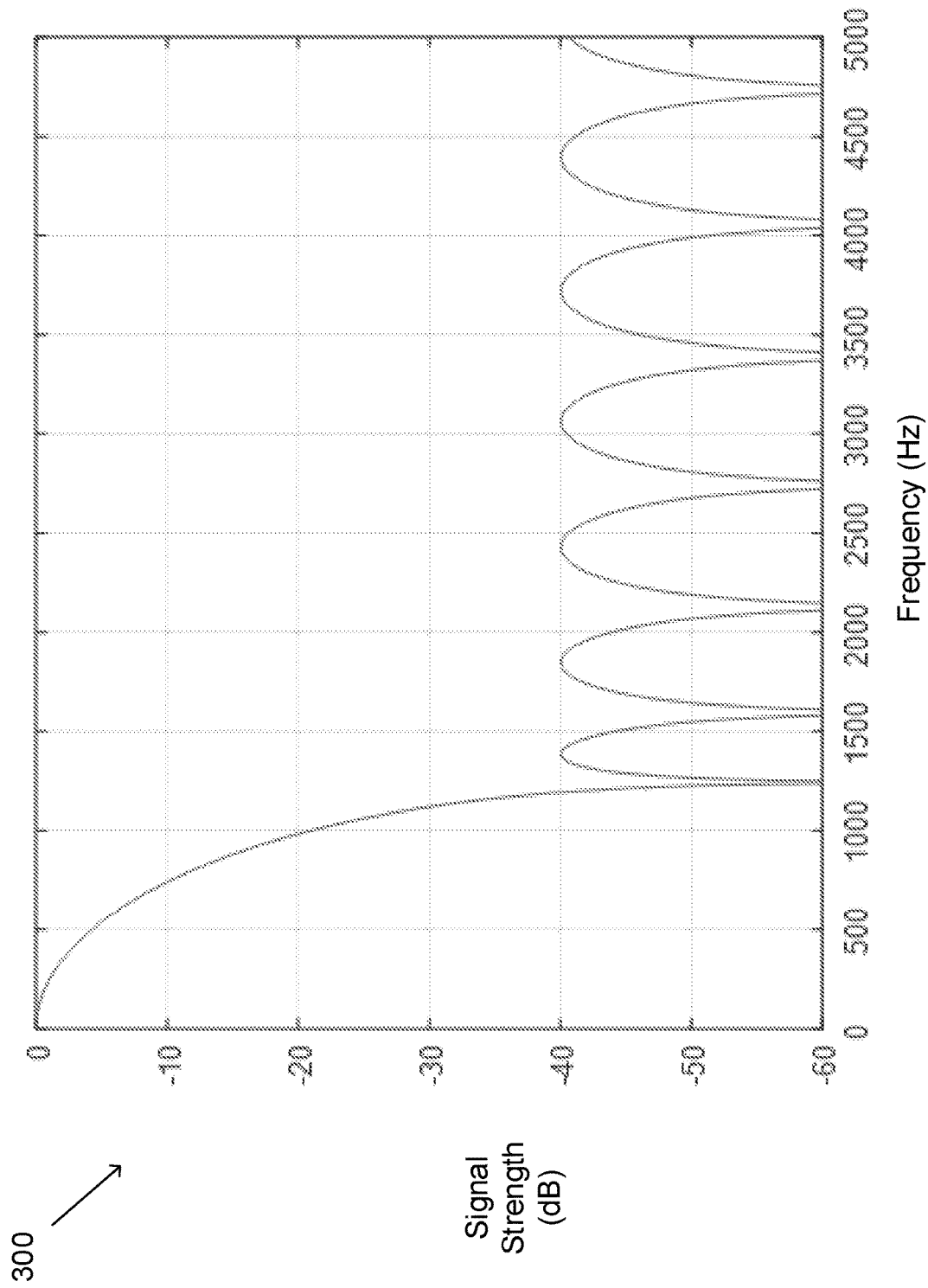
FIGS. 3-4 show example filters.

Turning to FIG. 3, an example graph 300 shows filter characteristics for shaping the signals transmitted by the transmitter coils 114a-n. In this example, a 69 tap Dolph-Chebychev filter is used to window the transmitter sine burst to restrict the bandwidth about the selected transmission frequency of each transmitter coil. Graph 300 shows the simulated frequency characteristic of the filter.

Figure 4:
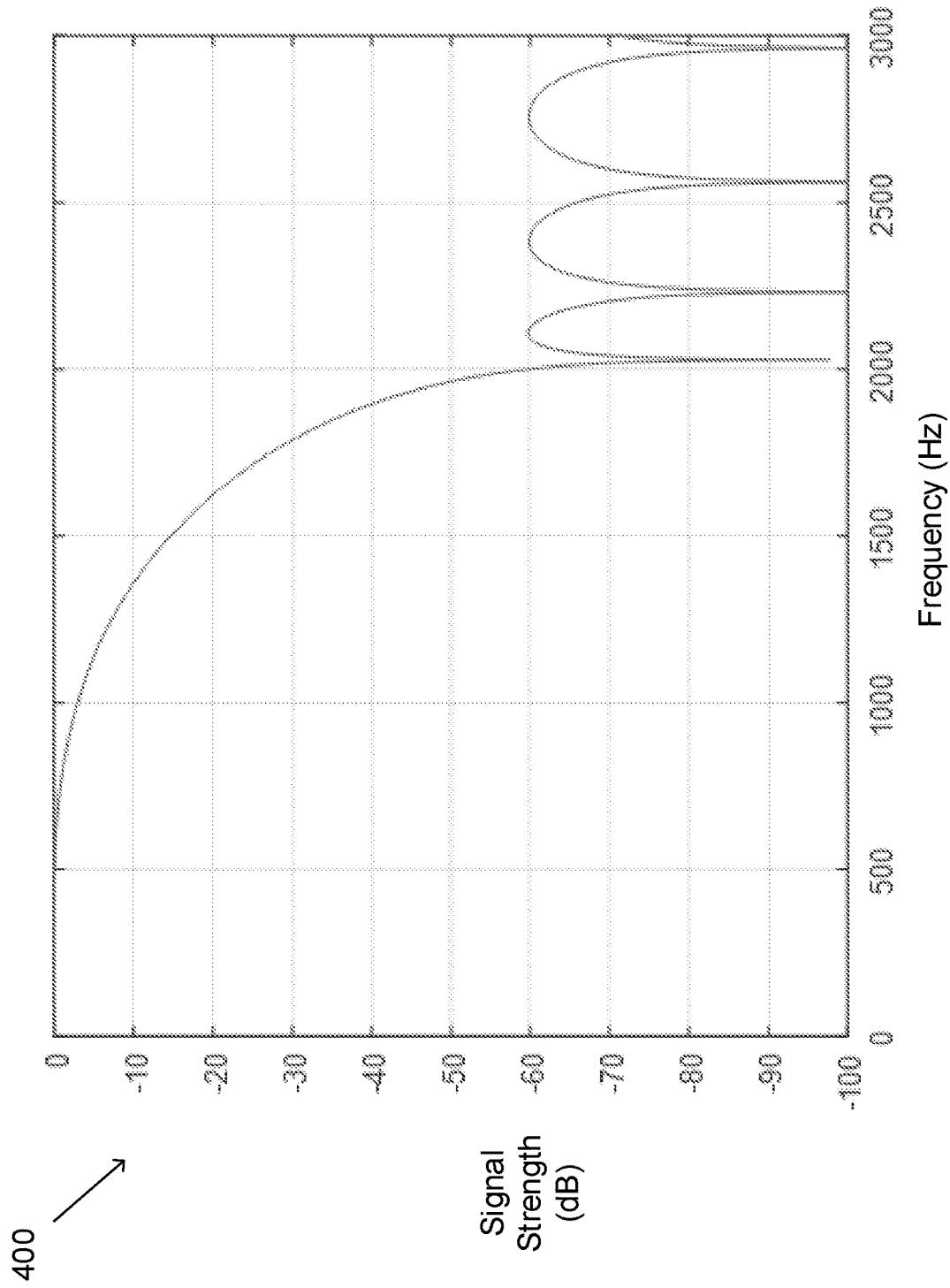

FIG. 4 shows an example graph 400 illustrating a frequency response of an envelope reconstruction device (e.g., a filter). The envelope reconstruction device includes circuitry configured to recover the carrier envelope signal and perform a filtering function to reconstruct the signal. Here, the device may include a demodulator to recover the carrier envelope signal. This can include synchronous or sinusoidal demodulation. In some implementations, the device is configured for demodulation for heterodyne operation. In another example, the device includes a diode rectifier. The filter function is applied to the demodulated signal. In an example, the envelope reconstruction filter can be part of the signal processing engine 216 of FIG. 2. The filter can be a low-pass filter that is used to reconstruct the demodulated signal envelope received at the sensor (e.g. sensor 106, 206 of FIGS. 1-2). The filter is used by the EMT system 100 to simulate a demodulated steady-state response of a portion of the signal processing for the EMT system 100. In this example, the demodulator low-pass output filter has a 3 dB cutoff frequency at about 1 KHz. The filter has a –60 dB response for frequencies over 2 KHz. FIG. 4 shows a simulated 99 tap filter frequency response of the filter.

Figure 5:
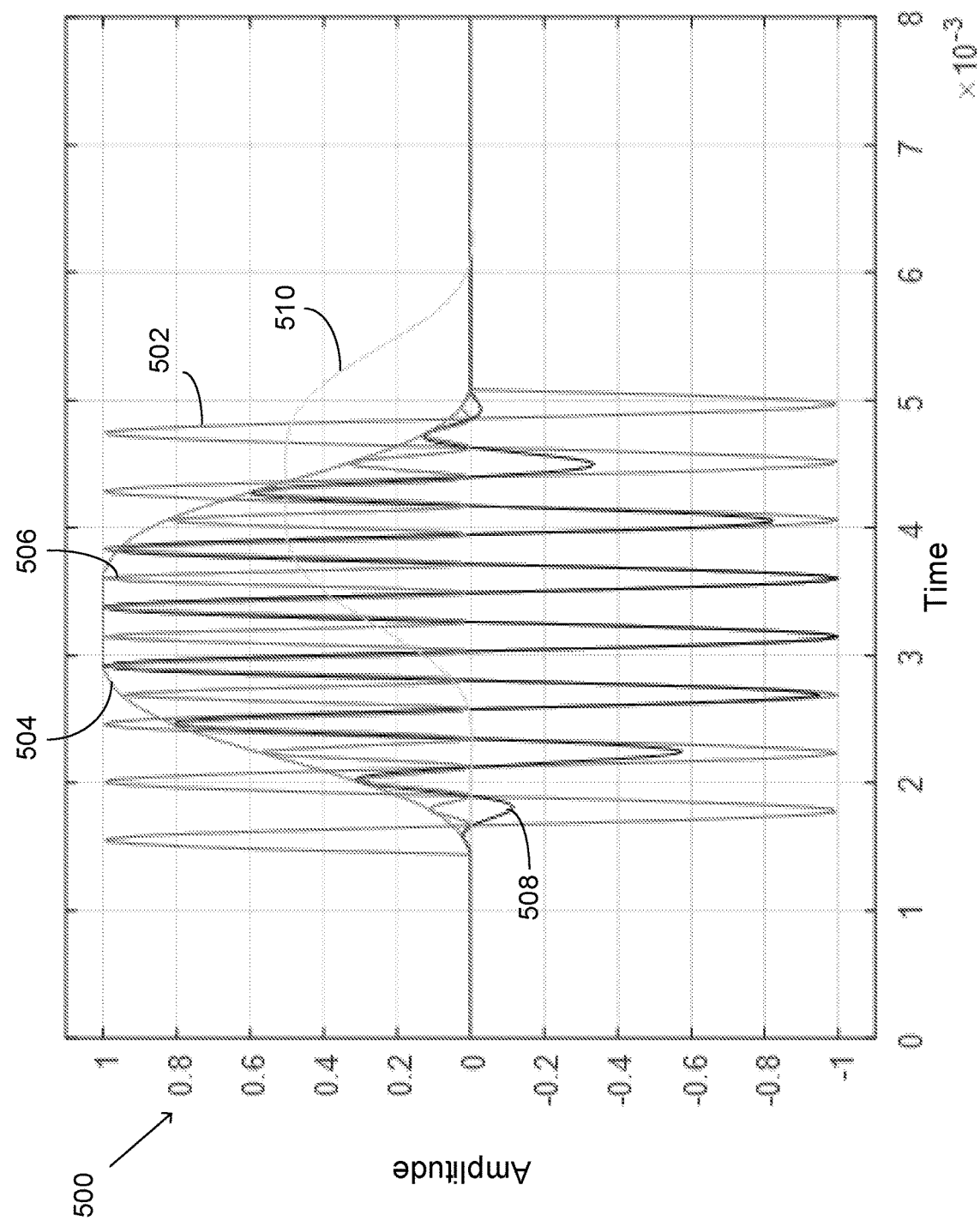
FIG. 5 shows an example of a shaped transmitted magnetic field signal.

FIG. 5 shows an example of transmitter signal derivation using the processing device 108 of the EMT system 100. The graph 500 shows a simulation of the transmitted shaped signal in addition to the demodulated signal. For graph 500, an eight-cycle sine burst at a center frequency of 2194.2851 Hz was used to generate in the simulation. A single transmitter pulse signal 502 before shaping is shown. This is also called the unwindowed sine burst. The same pulse is shown a signal 508 after being shaped by the windowing filter 504 step response (e.g., the Dolph-Chebychev filter of FIG. 3). The transmitter-windowed sine burst signal 506 is shown. The low-pass filtered demodulated signal 510 is also shown. For a unity amplitude sine wave, the demodulated steady-state response has 0.5 amplitude of the transmitted signal. Graph 500 shows how the signal of the transmitters 114a-n can be shaped and also demodulated to reduce or eliminate harmonic artifacts of the transmitted signal.

The result of application of the filter shows that the signal amplitude change is reduced on a per-cycle basis. Rather than a square wave control from an OFF state to an ON state, the amplitude of the magnetic signal is "ramped up" and "ramped down" according to the low-pass filter parameters so that there is not a sudden change in the amplitude of the signal from one cycle to the next cycle. Controlling the signal amplitude change in this way reduces the amplitude of the harmonic artifacts, as previously described.

Figure 6:
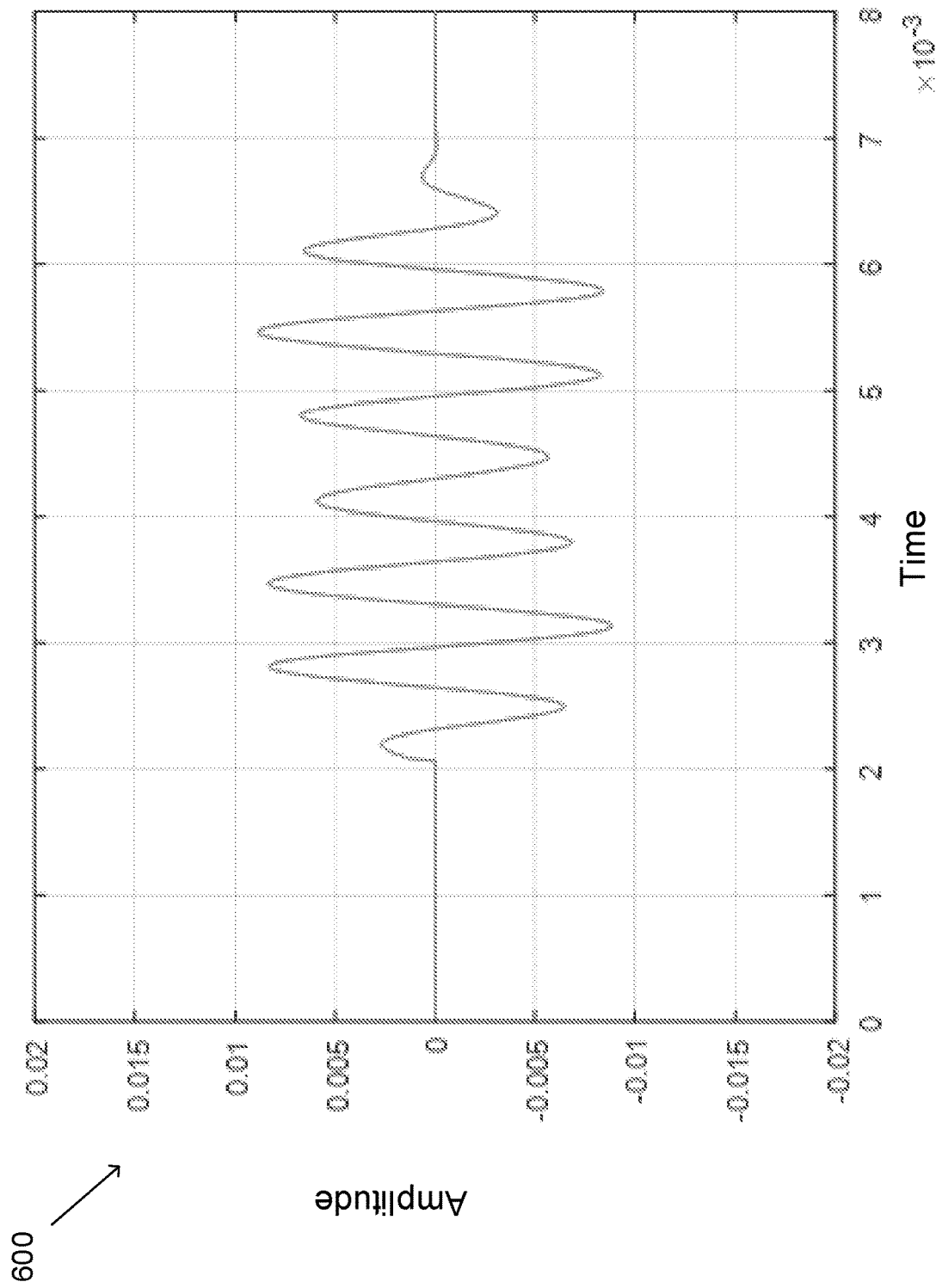
FIGS. 6-7 show examples of an electrocardiogram (EKG) response.
Figure 7:
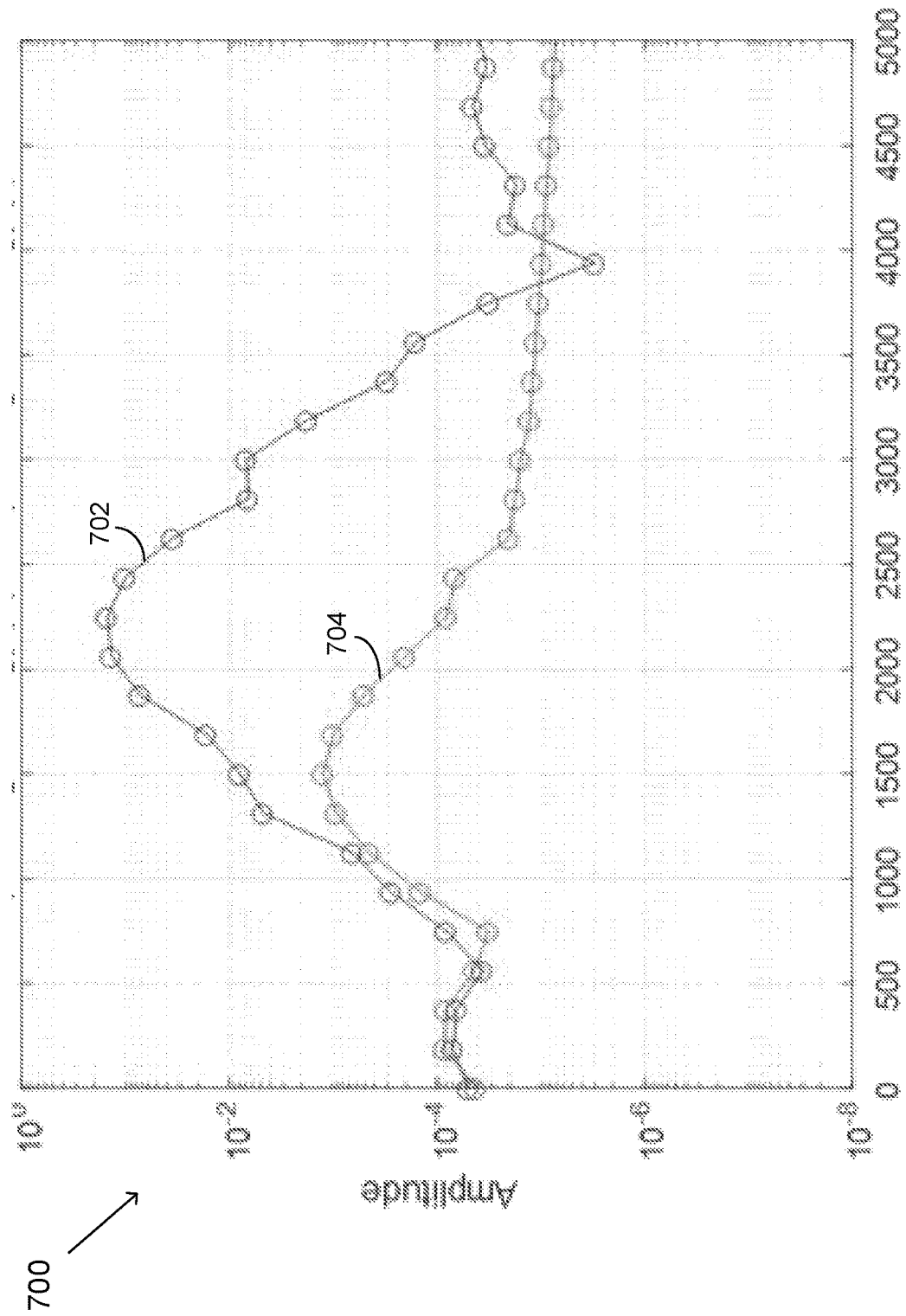

FIGS. 6-7 show respective graphs 600, 700 each illustrating an example electrocardiogram (EKG) filter response. As previously described, the EMT system 100 is configured to reduce or eliminate interference with biomedical instrumentation in the environment of the EMT system 100. The EKG example illustrates the reduction of interference with biomedical instrumentation using an EMT transmitter windowed ("shaped") sine burst. The EKG input filter response to the windowed transmitter signal is shown in graph 600 in the time domain. FIG. 7 shows a graph 700 representing the EKG response in the frequency domain. For this simulation, the same low pass filter characteristic shown in graph 400 was used to model the EKG filter responses of graphs 600 and 700. The resulting time domain ripple is below –40 dB. The signal shows eight cycles in which the center frequency is 2194.2851 Hz. The max ripple value was –42 dB. Graph 700 of FIG. 7 shows a fast-Fourier transform (FFT) of a transmitter windowed sine burst 702. Graph 700 also shows an EKG filter response 704. The frequency domain magnitude is mostly attenuated above 1,500 Hz range.

Figure 8:
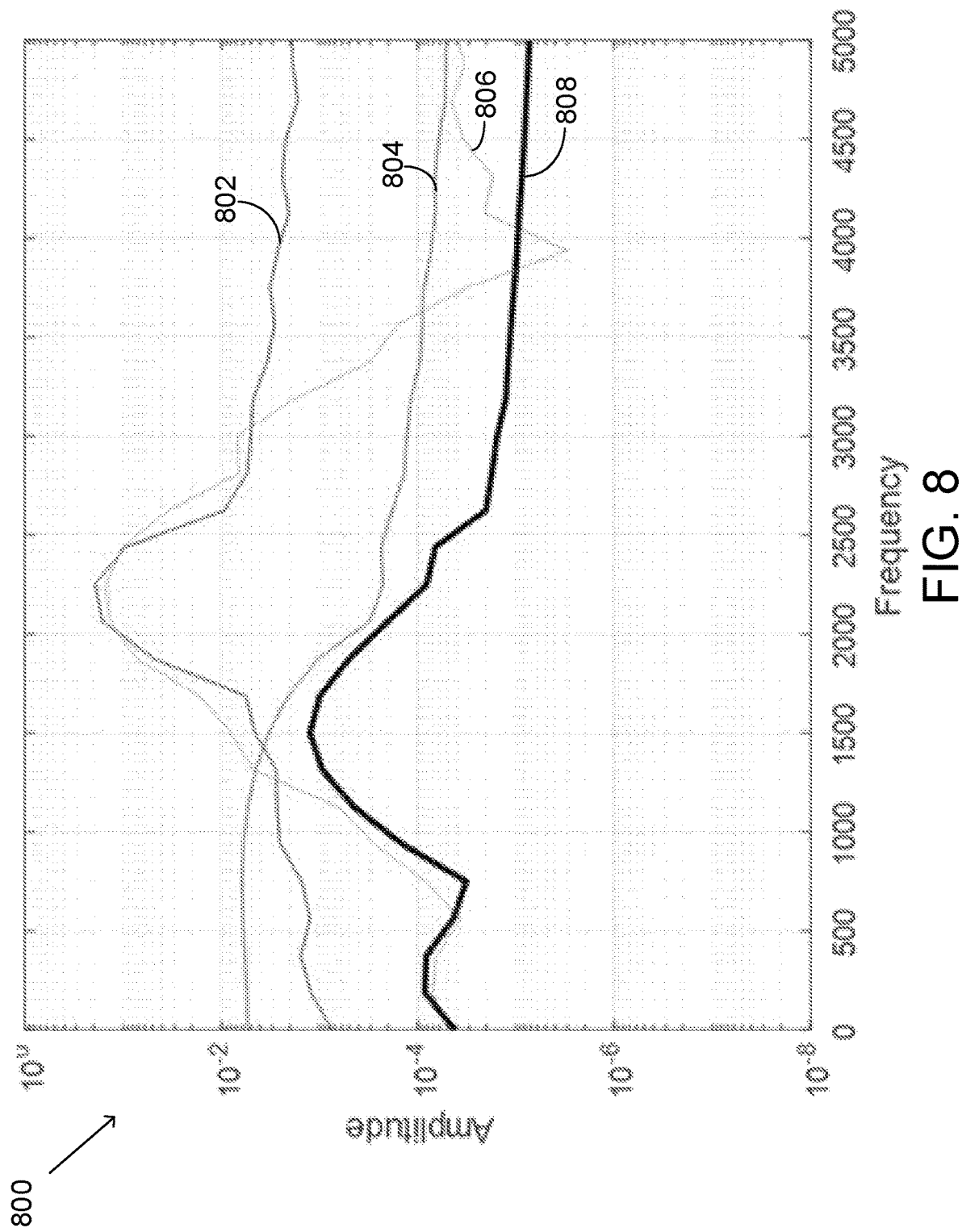
FIG. 8 shows a graph representing IMD reduction for a sensor of the EMT system of FIGS. 1-2.

FIG. 8 shows a graph 800 in which harmonic artifacts are reduced for receiving at a sensor (e.g., sensor 106 of FIG. 1 or sensor 206 of FIG. 2) is shown. Graph 800 shows a reduction in interference by magnetic field generators transmitting TDM-AC waveforms to minimize IMD in non-linear EMT sensors. In graph 800, the un-windowed sine burst signal 802 is shown. Graph 800 shows the response for a windowed (e.g., by a Dolph-Chebychev step response filter previously described) sine burst response 806. Graph 800 shows an EKG filtered un-windowed sine burst response 804. Graph 800 shows an EKG filtered windowed sine burst response 808. Here, the signal was received over eight cycles at a center frequency of 2194.2851 Hz. Comparing the frequency response of the unwindowed sine burst signal 802 with the windowed sine burst signal 806, graph 800 shows that a spectrum of the EMT field generator output is minimized for the signal 906 to reduce IMD effects in the receiver coil.

Figure 9:
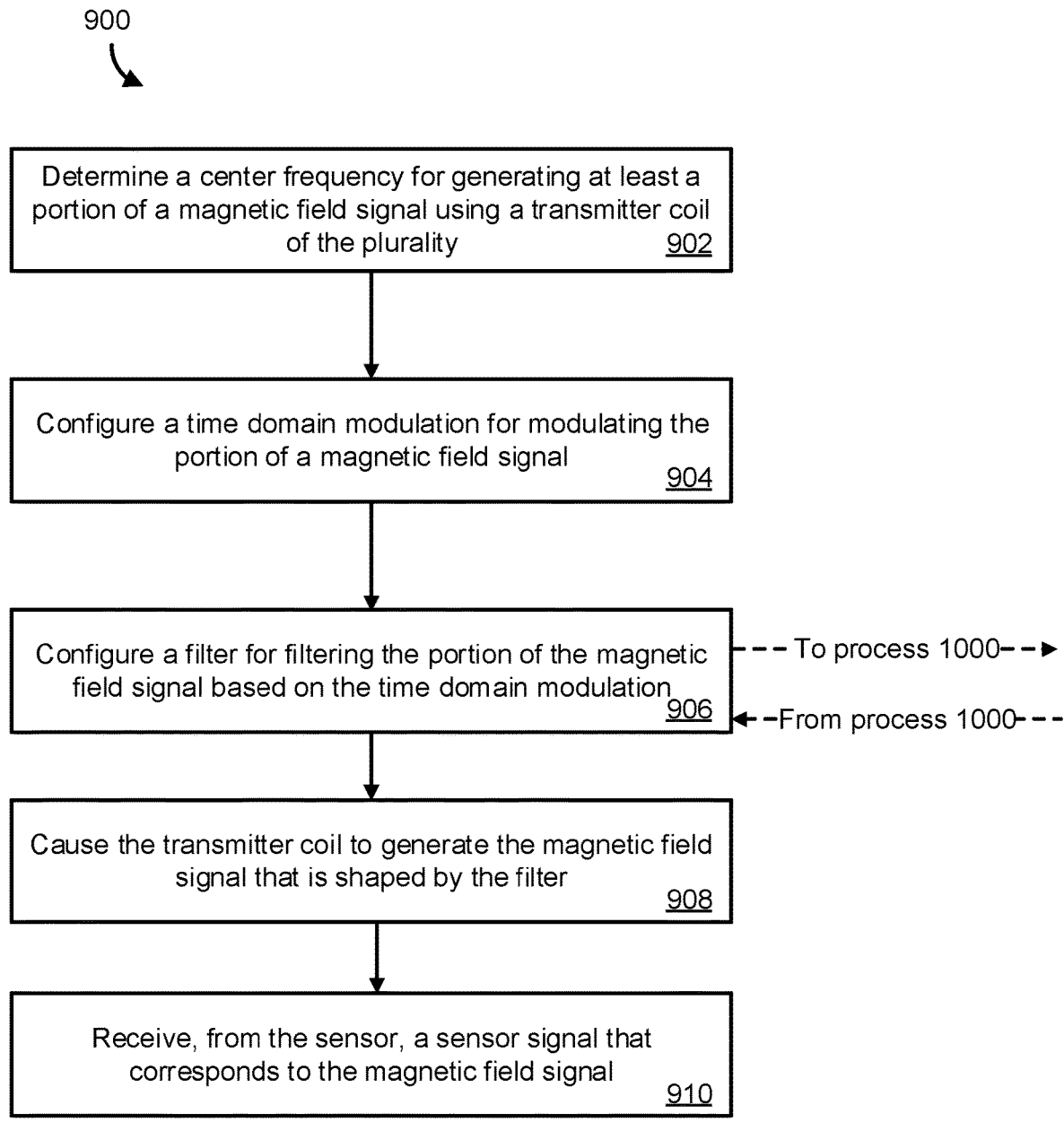
FIGS. 9-10 are flow diagrams that illustrate a process for interference reducing in an EMT system.

FIG. 9 shows a flow diagram showing a process 900 for interference reduction for a magnetic tracking system, such as the EMT system 100 and/or EMT system 200 previously described. The process 900 includes determining (902) a frequency for generating at least a portion of a magnetic field signal using a transmitter coil of the plurality of coils. A transmitter includes the plurality of coils, and the transmitter configured to generate magnetic field signals. The process 900 includes configuring (904) a TDM transmission of the EM signals from the transmitters. The process includes configuring (906) a filter for filtering the portion of the magnetic field signal based on the TDM. The filter is configured to shape the magnetic field signal to attenuate a harmonic artifact of the TDM signal. The process 900 includes causing (908) the transmitter coil to generate the magnetic field signal that is shaped by the filter. The process 900 includes receiving (910), from the sensor, a sensor signal that corresponds to the magnetic field signal. The sensor is configured to generate an output response indicative of the location of the sensor relative to the transmitter. The sensor includes the receiver and is configured to provide sensor signals that correspond to the magnetic field signals generated by the transmitter. The sensor signal is configured to produce an output response indicative of the location of the sensor relative to the transmitter based on the magnetic field signals generated by the transmitter.

Figure 10:

FIG. 10 shows a process 1000 for controlling the shape of the envelope based on data received or obtained that describes interference thresholds for one or more other devices or systems in the environment of the EMT system 100. Process 1000 includes obtaining (1002) threshold data representing a threshold interference level for one or more devices in an environment of the magnetic tracking system. Process 1000 includes configuring (1004) a filter for filtering the TDM control signal, the filter configured to shape each burst to reduce a harmonic artifact of the bursts below the threshold interference level of the threshold data. Process 1000 can include causing the transmitter coil to generate the shaped bursts of the magnetic field signal. The process 1000 can include receiving, from a sensor, a sensor signal that corresponds to the magnetic field signal, the sensor including the output response indicative of the location of the sensor relative to the transmitter. In some implementations, the threshold data are obtained from the one or more other devices during operation of the magnetic tracking system. The filter is configured to shape each burst for a next transmission in response to obtaining the threshold data. This can thus be a real-time or near real-time adjustment of the shaping of the signal envelope to reduce interference in one or more other systems below a specified threshold during operation of the EMT system 100.

The EMT system 100 described above can be implemented using software included on a computer-readable medium for execution on a computer (e.g., the processing device 108 of FIG. 1). For example, the software may form procedures in one or more computer programs that execute on one or more programmed or programmable computer systems (which may be of various architectures) each including at least one processor, at least one data storage system (including volatile and non-volatile memory and/or storage elements), at least one input device or port, and at least one output device or port.

Figure 11:
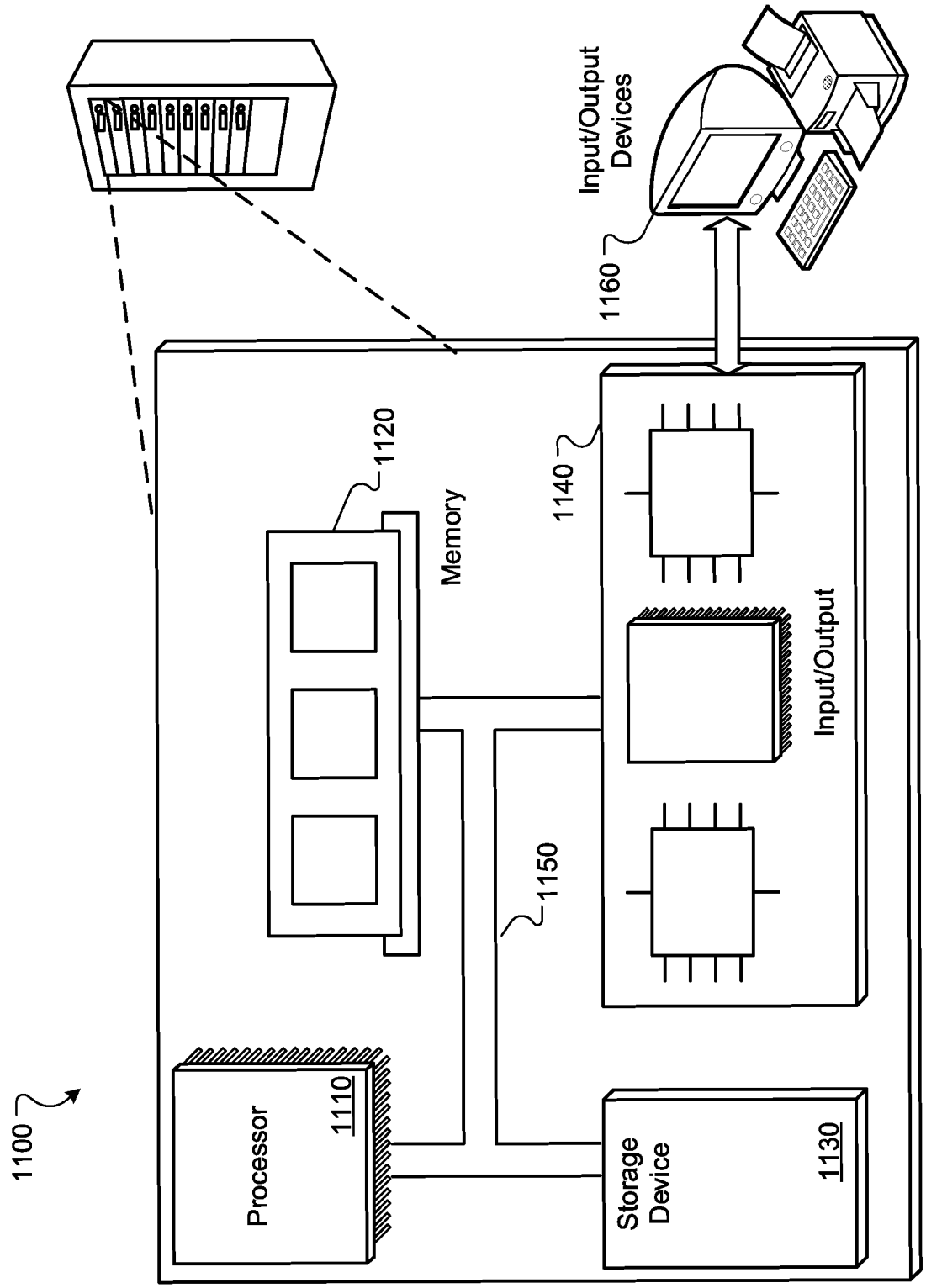
FIG. 11 is an example computing system.

FIG. 11 is a block diagram of an example computer system 1100. For example, the catheter tracking system can employ the processing device 108 of the EMT system 100 of FIG. 1 or processing device 208 EMT system 200 of FIG. 2. In some implementations, the computer system 1100 may provide visual information regarding the relative position and orientation of the tip of a tracked object. The computer system 1100 includes a processor 1110, a memory 1120, a storage device 1130, and an input/output device 1140. Each of the components 1110, 1120, 1130, and 1140 can be interconnected, for example, using a system bus 1150. The processor 1110 is capable of processing instructions for execution within the system 1100. In some implementations, the processor 1110 is a single-threaded processor. In some implementations, the processor 1110 is a multi-threaded processor. In some implementations, the processor 1110 is a quantum computer. The processor 1110 is capable of processing instructions stored in the memory 1120 or on the storage device 1130.

The memory 1120 stores information within the system 1100. In some implementations, the memory 1120 is a computer-readable medium. In some implementations, the memory 1120 is a volatile memory unit. In some implementations, the memory 1120 is a non-volatile memory unit.

The storage device 1130 is capable of providing mass storage for the system 1100. In some implementations, the storage device 1130 is a computer-readable medium. In various different implementations, the storage device 1130 can include, for example, a hard disk device, an optical disk device, a solid-date drive, a flash drive, magnetic tape, or some other large capacity storage device. The input/output device 1140 provides input/output operations for the system 1100. In some implementations, the input/output device 1140 can include one or more of a network interface devices, e.g., an Ethernet card, a serial communication device, e.g., an RS-232 port, and/or a wireless interface device, e.g., an 802.11 card, a 3G wireless modem, a 4G wireless modem, a 5G wireless modem, or another kind of interface. A network interface device allows the system 1100 to communicate, for example, transmit and receive data over a network. In some implementations, the input/output device can include driver devices configured to receive input data and send output data to other input/output devices, e.g., keyboard, printer and display devices 1160. In some implementations, mobile computing devices, mobile communication devices, and other devices can be used. For example, the catheter tracking system can use a computer interface to allow the operator to enter the planned procedure and indications for the catheter placement. The computer interface could be an example of an input/output device 1160. The catheter tracking system can also display visual information regarding the relative position and orientation of the catheter on an input/output device 1160.

Although an example processing system has been described, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. Sometimes a server is a general purpose computer, and sometimes it is a custom-tailored special purpose electronic device, and sometimes it is a combination of these things.

Certain features that are described that are described above in the context of separate implementations can also be implemented in combination in a single implementation. Conversely, features that are described in the context of a single implementation can be implemented in multiple implementations separately or in any sub-combinations.

The order in which operations are performed as described above can be altered. In certain circumstances, multitasking and parallel processing may be advantageous. The separation of system components in the implementations described above should not be understood as requiring such separation.

Other implementations not specifically described herein are also within the scope of the following claims.

What is claimed is:

1. A system comprising:
   a transmitter that includes a plurality of coils, the transmitter configured to generate magnetic field signals;
   a sensor that includes a receiver coil, the sensor configured to provide sensor signals that correspond to the magnetic field signals generated by the transmitter, wherein the sensor signal is configured to produce an output response indicative of a location of the sensor relative to the transmitter based on the magnetic field signals generated by the transmitter; and
   a computing device in communication with the transmitter and the sensor, the computing device configured to:
      determine a frequency for generating at least a portion of a magnetic field signal using a transmitter coil of the plurality;
      configure a time-division multiplexed (TDM) control signal for controlling transmissions of the magnetic field signal from the transmitter coil, the TDM control signal configured to cause the transmitter coil to periodically transmit bursts of the magnetic field signal at the frequency at a part of a TDM cycle different from other parts of the TDM cycle for one or more other transmitter coils of the plurality;
      configure a filter for filtering the TDM control signal, the filter configured to shape each burst by filtering a step function to reduce or prevent a harmonic artifact of the bursts, at the receiver coil, resulting from causing the transmitter coil to transmit the bursts of the magnetic signal periodically based on the TDM cycle;
      cause the transmitter coil to generate the shaped bursts of the magnetic field signal, the generation being periodic based on the TDM cycle, wherein the magnetic field signal comprises a TDM alternating current (TDM-AC) signal; and
      receive, from the sensor, a sensor signal that corresponds to the magnetic field signal, the sensor signal including the output response indicative of the location of the sensor relative to the transmitter.

2. The system of claim 1, wherein the computing device is further configured to:
   multiply the magnetic field signal with the step function to shape the bursts.

3. The system of claim 1, wherein the receiver coil comprises a core that has a relative magnetic permeability value greater than 1.

4. The system of claim 3, wherein the core comprises one of a ferrite material or a permalloy material.

5. The system of claim 1, wherein each coil of the plurality of coils in the transmitter is configured to generate a respective magnetic field signal at a respective frequency value that is different from other coils of the plurality.

6. The system of claim 5, wherein each burst is shaped by a filter signal to prevent interference of the magnetic field signal of a coil with adjacent measurement modalities of the other coils of the plurality.

7. The system of claim 1, wherein the sensor signal comprises a voltage that is generated based on interaction between the sensor and the magnetic field signal generated by the transmitter.

8. The system of claim 7, wherein a value of the voltage is indicative of at least one of an orientation and a position of the sensor relative to the transmitter.

9. The system of claim 1, wherein the filter is configured to reduce the harmonic artifact received at another electronic device in an environment to below a threshold level specified for the electronic device.

10. The system of claim 1, wherein the sensor is selected from a group comprising: a hall-effect sensor, a magnetoresistive sensor, a magneto-optical sensor, and a fluxgate magnetometer.

11. A method for reducing interference caused by a magnetic tracking system, the method comprising:
   determining, by a computing device, a frequency for generating at least a portion of a magnetic field signal using a transmitter coil of a plurality of transmitter coils of a transmitter;
   configuring, by the computing device, a time-division multiplexed (TDM) control signal for controlling transmissions of the magnetic field signal from the transmitter coil, the TDM control signal configured to cause the transmitter coil to periodically transmit bursts of the magnetic field signal at the frequency at a part of a TDM cycle different from other parts of the TDM cycle for one or more other transmitter coils of the plurality;
   obtaining, by the computing device, threshold data indicating a threshold interference level for one or more devices in an environment of the magnetic tracking system;
   configuring, by the computing device, a filter for filtering the TDM control signal, the filter configured to shape each burst by filtering a step function to reduce or prevent a harmonic artifact of the bursts, at a receiver coil, resulting from causing the transmitter coil to transmit the bursts of the magnetic signal periodically based on the TDM cycle, below the threshold interference level of the threshold data;
   causing, by the computing device, the transmitter coil to generate the shaped bursts of the magnetic field signal, the generation being periodic based on the TDM cycle, wherein the magnetic field signal comprises a TDM alternating current (TDM-AC) signal; and
   receiving, from a sensor including a receiver coil, a sensor signal that corresponds to the magnetic field signal, the sensor including an output response indicative of a location of the sensor relative to the transmitter.

12. The method of claim 11, wherein the threshold data are obtained from one or more other devices after a first transmission of the magnetic tracking system, and, in response to obtaining the threshold data, the filter is configured to shape each burst for a second transmission.

13. A method comprising:
   determining, by a computing device, a frequency for generating at least a portion of a magnetic field signal using a transmitter coil of a transmitter of a magnetic tracking system;
   configuring, by the computing device, a time-division multiplexed (TDM) control signal for controlling transmissions of the magnetic field signal from the transmitter coil, the TDM control signal configured to cause the transmitter coil to periodically transmit bursts of the magnetic field signal at the frequency at a part of a TDM cycle different from other parts of the TDM cycle for one or more other transmitter coils of the plurality;

configuring, by the computing device, a filter for filtering the TDM control signal, the filter configured to shape each burst by filtering a step function to reduce or prevent a harmonic artifact of the bursts, at a receiver coil, resulting from causing the transmitter coil to transmit the bursts of the magnetic signal periodically based on the TDM cycle, wherein the magnetic field signal comprises a TDM alternating current (TDM-AC) signal;

wherein the filter is configured to reduce the harmonic artifact received at another electronic device in an environment to below a threshold level specified for the electronic device;

causing, by the computing device, the transmitter coil to generate the shaped bursts of the magnetic field signal, the generation being periodic based on the TDM cycle; and receiving, from a sensor of the magnetic tracking system, a sensor signal that corresponds to the magnetic field signal, the sensor signal including an output response indicative of a location of the sensor relative to the transmitter.

14. The method of claim 13, wherein the method further comprises multiplying the magnetic field signal with the step function to shape the bursts.

15. The method of claim 13, wherein a receiver coil of the sensor comprises a core that has a relative magnetic permeability value greater than 1.

16. The method of claim 15, wherein the core comprises one of a ferrite material or a permalloy material.

17. The method of claim 13, wherein the sensor is selected from a group comprising: a hall-effect sensor, a magnetoresistive sensor, a magneto-optical sensor, and a fluxgate magnetometer.

18. The system of claim 1, wherein the computing device is further configured to:
determine a parameter value representing a magnetic property of a receiver core of a receiver coil; and
configure the filter for filtering the TDM control signal based on the parameter value for the receiver core of the receiver coil.

19. The system of claim 1, wherein configuring the filter for filtering the TDM control signal comprises adjusting a size of a signal envelope based on a determined threshold or a signal strength of a harmonic artifact for the magnetic field signal transmitted by the transmitter coil.

20. The method of claim 13, wherein the computing device is further configured to:
determine a parameter value representing a magnetic property of a receiver core of a receiver coil; and
configure the filter for filtering the TDM control signal based on the parameter value for the receiver core of the receiver coil.

21. The method of claim 13, wherein configuring the filter for filtering the TDM control signal comprises adjusting a size of a signal envelope based on a determined threshold or a signal strength of a harmonic artifact for the magnetic field signal transmitted by the transmitter coil.

* * * * *